United States Patent [19]

Knifton

[11] 4,169,853

[45] Oct. 2, 1979

[54] HOMOGENEOUS RUTHENIUM CATALYSTS USEFUL IN THE REDUCTION OF ORTHO-SUBSTITUTED NITROAROMATICS TO AMINES

[75] Inventor: John F. Knifton, Austin, Tex.

[73] Assignee: Texaco Development Corporation, White Plains, N.Y.

[21] Appl. No.: 875,477

[22] Filed: Feb. 6, 1978

[51] Int. Cl.$^2$ ............................................. C07C 85/11
[52] U.S. Cl. ............................... 260/575; 252/429 R; 252/431 C; 252/431 N; 260/570 R; 260/577; 260/580
[58] Field of Search ....................... 260/580, 575, 577

[56] References Cited

U.S. PATENT DOCUMENTS

| 3,832,401 | 8/1974 | Knifton et al. | 260/570.8 R |
| 3,906,045 | 9/1975 | Knifton et al. | 260/580 |

*Primary Examiner*—Winston A. Douglas
*Assistant Examiner*—John Doll
*Attorney, Agent, or Firm*—Thomas H. Whaley; Carl G. Ries; Bernard Marlowe

[57] ABSTRACT

This invention concerns the use of solubilized ruthenium-containing complexes in combination with quaternary ammonium hydroxides to effect the catalytic hydrogenation of certain classes of ortho-substituted mononitroaromatic substrates to their corresponding aryl amines.

3 Claims, No Drawings

HOMOGENEOUS RUTHENIUM CATALYSTS USEFUL IN THE REDUCTION OF ORTHO-SUBSTITUTED NITROAROMATICS TO AMINES

BACKGROUND AND SUMMARY OF INVENTION

Until comparatively recently homogeneous metal catalysts have been used primarily in the conversion of unsaturated organic molecules, particularly those with olefinic and acetylenic bonds, to their hydrogenated, oxygenated, hydroformylated, and/or isomerized derivatives. Particularly favored were linear olefins both of the alpha and internal type. Homogeneous catalysts have become especially popular in these reactions because they generally offer several practical advantages over comparable heterogeneous catalysts. These advantages include one or more of the following, viz. faster rates of reaction, improved selectivities to desired product or products, resistance to common catalyst poisons such as sulfur compounds, and milder conditions of operation.

While solubilized catalysts have found special applications in the derivatization of olefins, far less has been published on their use in converting other functional groups not containing carbon-carbon multiple bonds. Recently, novel processes have been disclosed which enable homogeneous catalytic techniques to be applied to the selective hydrogenation of nitro($-NO_2$) compounds. Important applications for this technique include the reduction of nitroparaffin substrates to their paraffinic amines*, the selective hydrogenation of certain classes of mono and polynitroaromatics to their corresponding aromatic amines and nitroamines, and the sequential hydrogenation of nitroaromatic mixtures, e.g., nitroaromatic-polynitroaromatic mixtures*. Not only are selectivities and yields good, but the resultant paraffinic or aromatic amines can be recovered from the crude reaction mix by standard experimental procedures used in amine isolation and purification.

*Knifton et al, U.S. Pat. No. 3,766,271 (1973)
**Knifton et al, U.S. Pat. No. 3,832,401 (1974)
***Knifton et al, U.S. Pat. No. 3,903,167 (1975)

While in the case of nitroaromatic stocks, however, said processing is effective in hydrogenating broad classes of nitroaromatics, including mononitro-ortho-substituted polyalkyaromatics, such as 2-nitro-m-xylene**, it is not generally effective for the selective hydrogenation of other classes of ortho-substituted nitroaromatics that contain nonalkyl ortho-substituents. Likewise, many older catalytic hydrogenation techniques advanced in the open literature are unsuited for the selective reduction of ortho-substituted mononitroaromatics on account of cleavage of functional groups, cyclization and incomplete reduction.

**Knifton et al, U.S. Pat. No. 3,906,045 (1975)

Applicants disclose herein then a homogeneous hydrogenation technique employing solubilized ruthenium-containing complexes in combination with quaternary ammonium hydroxides to effect the selective hydrogenation of certain classes of nitroaromatic substrates containing bulky and/or reactive ortho-substituents, to their corresponding hindered aromatic amines. Alternative cleavage and cyclization reactions and incomplete reduction are not important with this class of catalyst, consequently selectivity to desired amine generally ranges from 85 to 100%.

By selectivity, as defined herein, is meant the efficiency in catalysing a desired conversion relative to other undesired reactions, in this instance reduction of nitro ($NO_2$) groups on aromatic rings to the desired and corresponding amines. Selectivity is usually expressed as a percentage factor representing the amount of the amine formed, divided by the amount of starting nitroaromatic converted. Likewise, amine yield here refers to the fraction of amine formed, divided by the amount of nitroaromatic charged.

In view of the aforementioned deficiencies of the existing catalysts when applied to the hydrogenation of certain classes of hindered nitroaromatics, the catalysts of this invention represent a substantial advance in the art. Particularly, said catalysts satisfy in most instances the following objects:

(a) The ability to hydrogenate the nitro ($NO_2$) function of nitroaromatics containing a variety of other functional groups including alkyl groups, halo, aryl, benzyl, acetyl, alkoxyl, halogenated alkyl, substituted amino, amino, carboxyl and alkylthio substituents.

(b) The ability to selectively hydrogenate nitroaromatic substrates containing bulky and/or reactive ortho-substituents wherein each $NO_2$-group to be hydrogenated is bonded via a C—N bond to an aromatic ring system, and one or both of the carbon atoms of the aromatic ring system adjacent to the carbon of the C—N bond are also bonded to bulky and/or reactive substituents (R and R' in eq 1) said substituents being selected from the functional groups including alkyl, halogenated alkyl, alkoxyl, acetyl, halo, amino and alkylated amino substituents, together with mixtures thereof.

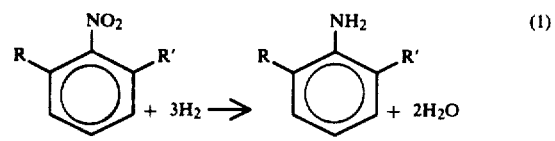

(1)

Other objects will become apparent to those skilled in the art after a perusal of this application.

In practice, the above objects, among others, will be achieved by the following procedure or minor modifications thereof.

PROCESS EMBODIMENTS

In the broadest contemplated practice of this invention:

(a) The nitroaromatic substrates to be reduced are admixed in the absence of oxidizing conditions, with at least a catalytic amount of a ruthenium-containing catalyst complex and a quaternary ammonium hydroxide in a substantially non-aqueous, inert solvent media to form a reaction media, and, (b) Said reactive mixture is heated from at least 20° C. and upwards under superatmospheric pressures in the presence of at least a stoichiometric quantity of hydrogen (with respect to nitroaromatic substrate) until substantial reduction of the nitroaromatics to the corresponding amines takes place.

In the favored practice the nitro groups of mononitroaromatic substrates containing one or more ortho-substituents are selectively hydrogenated to the corresponding amines by the process of:

(a) Admixing each ortho-substituted nitroaromatic substrate to be reduced with at least a catalytic amount of one or more ruthenium-containing catalyst complex in oxidizer free, non-aqueous solvent media to form a reaction mixture.

(b) Introducing into said reaction mixture an excess of quaternary ammonium hydroxide and at least sufficient hydrogen gas to hydrogenate the nitro groups of said substrates to the corresponding amines, at superatmospheric pressures ranging from about 100 psi to about 2000 psi.

(c) Heating said pressurized reaction mixture between about 20° to about 160° until said nitroaromatic substrates are reduced, and (d) Isolating said amine contained therein.

In order to aid in the full understanding of the inventive concept, the following additional disclosure is submitted:

A. Nitroaromatic Substrates

Any aromatic substrate containing from 6 to 30 carbon atoms, or more, and containing at least one nitro ($NO_2$) group per molecule may be employed. These include the mononuclear mononitroaromatics such as nitrobenzene, nitrotoluenes, nitroxylenes as well as the dinuclear, trinuclear and higher (polynuclear) mono nitroaromatics such as 1-nitro-naphthalene and 5-nitroanthracene. The di- and trinitro aromatics, that is di-, trinitromononuclear compounds such m-dinitrobenzene and its congeners may also be substrates, in addition to di-, tri- and poly-nitropolynuclear aromatics such as 1,9-dinitronaphthalene and its homologues and, where they are available, nitro steroids.

More particularly, however, this invention is directed to the hydrogenation of nitroaromatic substrates containing bulky and/or reactive ortho-substituents (eq 1). Here said $NO_2$-group to be hydrogenated is bonded via a C—N bond to an aromatic ring system and one or both of the carbon atoms of the ring system adjacent to the C—N bond are also bonded to bulky and/or reactive substituents. Suitable ortho-substituents include one or more of the following: alkyl groups, halogenated alkyl, alkoxyl, acetyl, carboxyl, aryl, benzyl, halo, substituted amino, amino and alkylthiol substituents, together with mixtures thereof.

Examples of suitable nitroaromatic substrates containing bulky and/or reactive ortho substituents that may be selectively hydrogenated by the process of this invention include: o-nitroaniline, N-methyl-o-nitroaniline, N,N-dimethyl-o-nitroaniline, 2-nitro-m-phenylenediamine 4-nitro-m-phenylenediamine, 2-nitro-p-phenylenediamine, α,α,α-trifluoro-o-nitrotoluene, 1-chloro-2-nitrobenzene, o-nitroanisole and o-nitroacetophenone. Evidence for the selective hydrogenation of these nitroaromatic substrates may be found in the subsequent examples 1-13. Said nitroaromatic substrates can be in the form of nitrated aromatics and, as such, may contain substantial quantities of non-nitrated aromatics or their mixtures, neat or containing other inert solvents or diluents such as paraffins, ethers and the like. When selectivity to a particular aromatic amine is not required mixtures of isomers, or mixtures of mono, di- and trinuclear substrates containing 1 to 3 nitro groups may also be employed.

B. Inert Diluent and Solvents

The novel reduction process can be run most readily in the presence of sufficient inert diluent to form a homogeneous single phase reaction mixture. Since a homogeneous, or uniform, reaction mixture offers the most convenient vehicle in which to rapidly reduce the nitroaromatics to amines in good yield, the use of inert solvent is normally employed. Generally speaking, any organic liquid in which the nitroaromatic substrate and catalyst is soluble and which is inert to reduction under the conditions of the inventive process, can be used as a diluent. These include the alkyl ethers, such as diethyl ether, the $C_1$ to $C_6$ alkanols, the hydroxylated ethers, chlorinated hydrocarbons such as methylene chloride, aromatics such as benzene, toluene and xylene, as well as their mixtures with or without added alkaline or acid agents.

C. Reducing Atmosphere

Insofar as can be determined, the homogeneous catalyst, possibly in some intermediate, more active form, abstracts hydrogen from the environmental, hydrogen atmosphere. While nitrogen, methane, ethane, or inert gases such as helium, argon or neon may be present in small proportions, (less than 30% by volume) without adversely effecting conversions or yields, their presence appears to offer no concurrent advantages and, therefore, is to be avoided.

Ordinarily, a reaction vessel capable of being pressurized, agitated, heated and cooled is charged with all of the components of the reaction mixture, nitroaromatic, catalyst system, solvents, etc. These components either individually or collectively are flushed with inert gas such as argon or nitrogen because of their known sensitivity to oxidizing agents such as air. The residual flushing or purging of inert gaseous environment is conveniently accomplished with hydrogen or nitrogen and the reaction mixture is pressurized initially to the desired extent and heated in a substantially hydrogen atmosphere until the desired reduction to aromatic amine takes place.

D. Reduction Temperature

The reaction temperature for reduction is in many ways quite flexible. At temperatures below about 20° C., however, the rate of reduction of substrate to the amine is quite slow, while at temperatures much above 160° C. yields fall off sharply, probably due to catalyst decomposition, and for this reason those temperatures in excess of 160° C. are to be avoided. Since good results have been obtained between 20° C. and 160° C. these are favored. Inasmuch as the best yields of amine have been obtained at reduction temperatures between about 50° C. and 135° C. at superatmospheric pressures, when the preferred homogeneous ruthenium complexes are used as catalysts, these temperatures represent the preferred temperature range.

E. Reduction Pressures

Pressures of hydrogen greater than atmospheric (O psig) are required to obtain reasonable rates of reduction at reaction temperatures above 35° C. Superatmospheric hydrogen pressures ranging from about 100 psig to about 2000 psig, coupled with temperatures of about 50° C. to 135° C. consistently give the best yields within reasonable reaction times and for this reason are preferred.

F. Reaction Times for Substantial Reduction

The time required for substantial reduction of the nitroaromatics to the corresponding amines is a variable, dependent primarily upon the temperature and pressure employed, the particular nitroaromatic substrate to be reduced and the ratio of substrate to catalyst system employed, among other factors. Ordinarily the reaction times will vary between about 10 minutes to 24 hours. In most instances, times ranging from at least about 1 hour to about 8 hours under the preferred conditions of temperature and pressure are required for substantial reduction and these reaction times represent the preferred range of reaction times.

G. Catalyst System

The homogeneous catalyst combinations of this inventive process that are particularly suited for the selective catalytic hydrogenation of nitroaromatic substrates containing bulky and/or reactive ortho-substituents consist primarily of a class of ruthenium-containing complexes or salts in combination with various quaternary ammonium hydroxides.

Insofar as is known, any ruthenium compound or complex may be employed provided that two conditions are satisfied:

(1) that the catalytic entity is stable under the reaction conditions employed and it exercises the desired reductive activity, and (2) that the ruthenium catalyst is soluble and does not precipitate prior to substantial reduction of the nitroaromatic.

Preferably, but not necessarily, the metallic compound as typified by ruthenium is one which contains displaceable ligands. However, in some instances it is desirable to use a solvating agent to convert the ruthenium compound to a more soluble form. The solvating agent usually comprises a polar solvent having an active hydrogen atom preferably contained in a hydroxyl group. Suitable solvating agents include the lower alkanols such as ethanol and propanol, cycloaliphatic or aromatic alcohols and phenols, as well as the mixtures of these alkanols and aromatics either in the neutral or alkaline state.

It is not essential that all of the ruthenium compound shall be in solution at the beginning of the reduction provided that at least a catalytic amount is present. A catalytic amount as defined herein refers to an amount sufficient under the appropriate combination of temperature and pressure parameters to initiate the desired reduction. In this instance, if at least 0.0001 gm atom, but preferably at least 0.001, of ruthenium per mole of nitroaromatic are present, catalysis will take place. Higher ratios of catalyst to substrate give more rapid conversions although ratios of 0.1 or more are disadvantageous in that they are costly and entrap or entrain product, unnecessarily complicating isolation and purification. Preferably the ruthenium compound is used in the form of a complex containing one or more $\pi$-bonding ligands such as carbonyl (CO), substituted carbonyl, nitrosyl, or a ligand containing a donor atom of Group IVB*, Group VB or Group VIB of the Periodic Table such as triphenylphosphine, triethylphosphine, pyridine, triphenylarsine, diethylsulphide, trichlorostannate(II), and the like. These ligands may or may not be displaced during hydrogenation. While no mechanism is postulated or is relied upon for patentability, it is believed that the catalysts, as typified by ruthenium, form hydrido species which are soluble in the liquid reaction medium used. As disclosed above, the neutral ligand may be a tertiary, organic substituted, phosphine or arsine such as $PR_3$, $AsR_3$, where P and As represent their respective elements and R is a symbol for hydrocarbyl radical, particularly alkyl, aryl, alkylated aryl, or mixtures thereof. One or more of the radicals may be the same or different at any particular time. Suitable anionic ligands include Cl—, Br—, CN—, NCO, $CH_3COO$—, with the halogens being preferred.
*Derived from "Advanced Inorganic Chemistry", by F. A. Cotton and G. Wilkinson, 3rd Ed. (1972).

Illustrative ruthenium complexes which function effectively in the basic reaction media include $RuHCl(PPh_3)_3$*, $RuCl_3(PPh)_3$(solvent), $RuCl_3[S(C_2H_5)_2]_3$, $RuCl_2(PPh_3)_3$, $RuCl_3$-(NO)($PPh_3)_2$, $RuCl_2(CO)_2(PPh_3)_2$, $RuCl_3(AsPh_3)_2$, $Ru(CF_3COO)_2$-(CO)(PPh_3)_2$, $RuCl_3.XH_2O$, $Ru(CO)_3[AsPh_3]_2$, $H_2Ru(PPh_3)_4$, $Ru_3(CO)_{12}$, $Ru_4H_4(CO)_{12}$, $Ru(CH_3COO)_3$, $RuCl_3[P(p-CH_3.Ph)_3]_2$, $RuH(CH_3COO)(PPh_3)_3$, $[RuCl_2(CO)py_3]$, $RuHCl(CO)[PC_6H_5(CH_3)_2]_3$, $RuCl_2[As(C_2H_5)_3]_3$, $RuBr_2(PPh_3)_3$, $Ru(CO)_3(PPh_3)_2$, $RuCl_2(PPh_3)_4$, $RuCl_2[As(PPh_3)_3]_3$, $Ru(Acet)_3$*, $[RuCl_2(CO)_3]_2$ and $[Ru(CO)_2Cl_2 (SnCl_3)_2]^{2-}$.
*Where Ph is a symbol for the phenyl radical $C_6H_5$.
**Where py is a symbol for pyrdine, $C_5H_5N$.
***Where Acet is a symbol for the acetylacetonate group ($CH_3COCHCOCH_3$)

The quaternary ammonium hydroxide components required for selective hydrogenation of nitroaromatics with bulky and/or reactive ortho substituents include both the alkyl and aryl quaternary ammonium hydroxides, together with mixed aryalkyl ammonium hydroxides. More specifically they include tetramethylammonium hydroxide, tetraethylammonium hydroxide, Triton-B(N-benzyltrimethylammonium hydroxide), tribenzylmethylammonium hydroxide, tetra-n-butylammonium hydroxide, N-benzyltriethylammonium hydroxide, dimethyldioctylammonium hydroxide, trimethyloctadecenylammonium hydroxide, trimethyldodecylammonium hydroxide and trimethyloctylammonium hydroxide.

Said bases may be added to the reactive mixture in pure form, or solubilized in a suitable non-aqueous diluent. Evidence of the value of said quaternary ammonium bases in selectively hydrogenating nitroanilines may be found in the comparative data summarized in Table I, infra.

H. Experimental Procedure

The hydrogenation process of this invention is ordinarily performed as follows:

A conveniently sized reactor fitted with glass liner, gas inlet, condenser, stirring, heating and pressurizing means, is charged with the ruthenium catalyst solution, preferably deoxygenating during charging, and containing the nitroaromatic substrate, quaternary ammonium base and inert solvent. Deoxygenation can be accomplished by a hydrogen or nitrogen flush of the reaction mixture. The agitated reaction mixture is sealed and heated to above 20° C. under superatmospheric pressure provided by hydrogen under pressure.

Work-up of the product mixture is as follows:

After hydrogen absorption has substantially ceased, indicating completion of the reduction, the pressurized reactor is cooled and excess gas bled off. The reaction mixture containing aryl amine product, catalyst and volatiles have the volatiles evaporated off under reduced pressure and the spent catalyst is filtered or removed by centrifugation. The reaction mixture contained in the filtrate is then recovered by one or more of the methods used to separate amines from contaminants. For example, the amine can be isolated by preparative gas chromatography (gc), alternatively it may be steam distilled or extracted with mineral acid. In the latter case, the amine salt is converted (sprung) to the free amine by neutralization with a basic material.

In any event, the amine product can be further purified or used as obtained, dependent upon product application. In general, the amines are identified by elemental analyses, gas chromatography (gc), infrared spectra (ir) and/or nuclear magnetic resonance (nmr) spectra.

EXAMPLE 1

The Hydrogenation of N,N-Dimethyl-O-Nitroaniline

To a suitable glass-lined autoclave-type reactor provided with pressurizing, heating, cooling, agitation and distillation means, containing 45 ml of a deoxygenated 1:1 equi-volume mixture of benzene and ethanol is charged 2.09 gm (12.5 mmole) of N,N-dimethyl-o-nitroaniline and 0.12 gm (0.125 mmole) of tris(triphenylphosphine)ruthenium(II) chloride. The mixture is stirred under a nitrogen blanket to dissolve solids and a 5.68 gm solution of tetramethylammonium hydroxide (24%, 15 mmole) in methanol added. The reaction mixture is sealed, pressurized to 1200 psi with hydrogen and heated to 120° C. for five hours with stirring.

Upon cooling and bleeding off excess gas, the 48 ml of dark-brown liquid product is recovered from the reactor, and the solvent system removed by fractional distillation under reduced pressure (1 cm Hg). N,N-Dimethyl-o-phenylenediamine is recovered from the deep-brown residual liquid (2.1 gm) by preparative glc and identified by elemental, ir and nmr analyses. Crude liquid product analyses typically show:

| | |
|---|---|
| Conversion of N,N-dimethyl-o-nitroaniline | >95% |
| Selectivity of N,N-dimethyl-o-phenylene-diamine | 85% |
| Recovery of ruthenium in solution | >95% |

EXAMPLE 2

The Hydrogenation of α,α,α-Trifluoro-O-Nitrotoluene

Following the procedure of Example 1, 2.39 gm of α,α,α-trifluoro-o-nitrotoluene (12.5 mmole) and 0.12 gm (0.125 mmole) of tris(triphenylphosphine)ruthenium(II) chloride are combined with 45 ml of an equivolune mixture of benzene, methanol, the mixture stirred under a nitrogen blanket and 5.68 gm of tetramethylammonium hydroxide (24%, 15 mmole) in methanol added. The mixture is sealed, pressured to 1200 psi with hydrogen, and heated to 120° for five hours with stirring.

After cooling and bleeding off excess gas, the 51 ml of dark-brown liquid product is recovered from the reactor. There is no evidence for solid precipitate at this stage. Forty five ml of the liquid product is subject to fractional distillation under reduced pressure. α,α,α-Trifluoro-o-toluidine is recovered from the reddish-brown liquid residue (7 ml) by preparative gc and identified by elemental, ir and nmr analyses. Crude liquid product analyses typically show:

| | |
|---|---|
| Conversion of α,α,α-trifluoro-o-nitrotoluene | >95% |
| Selectivity to α,α,α-trifluoro-o-toluidine | 92% |
| Recovery of ruthenium in solution | >95% |

EXAMPLE 3

The Hydrogenation of N-Methyl-O-Nitroaniline

To the glass-lined autoclave-type pressure reactor of Example 1 containing 45 ml of a deoxygenated 1:1.25 volume mixture of ethanol and benzene is charged 1.90 gm (12.5 mmole) of N-methyl-o-nitroaniline and 0.12 gm (0.125 mmole) of tris(triphenylphosphine)ruthenium(II) chloride. The mixture is stirred under nitrogen to produce a tea-brown clear liquid, with no residual solids. Tetramethylammonium hydroxide (5.68 gm, 24% Me$_4$NOH) in methanol is added, and the opaque, reddish-brown liquid mixture sealed, pressured to 1200 psi with hydrogen, and heated to 120° for 5 hours with stirring.

When cooling and bleeding off excess gas, the 48 ml of purple liquid is recovered from the reactor. There is no evidence of solid precipitation at this stage. N-Methyl-o-phenylenediamine is isolated by preparative glc and identified by elemental, ir and nmr analyses. Crude liquid product analyses typically show:

| | |
|---|---|
| Conversion of N-methyl-o-nitroaniline | >95% |
| Selectivity of N-methyl-o-phenylenediamine | 60% |
| Recovery of ruthenium in solution | >95% |

EXAMPLES 4–11

The Hydrogenation of O-Nitroaniline

Following the procedure of Example 1, hydrogenation of o-nitroaniline (1.73 gm, 12.5 mmole) is carried out in the presence of tris(triphenylphosphine)ruthenium(II) chloride catalyst (0.12 gm 0.125 mmole) in benzene, ethanol (45 ml). Initial pressuring is to 1200 psi with hydrogen, operating temperature is 120° C. The experimental variable is the presence or absence of various added bases. Results are summarized in Table I. It may be noted that:

a. No significant conversion of o-nitroaniline is observed in the absence of added base, using benzene-ethanol alone as diluent (Example 4) whereas the corresponding p-nitroaniline substrate, with no bulky ortho substituents, is readily hydrogenated to p-phenylenediamine in 94% selectivity under similar conditions (Example 5).

b. Conversion of o-nitroaniline is not observed in the presence of added organic tertiary nitrogen base, such as quinoline (Example 6)

c. o-Phenylenediamine is readily obtained in good yields when hydrogenation of o-nitroaniline is effected in the presence of quaternary alkyl and aryl ammonium hydroxides, viz:
tetramethylammonium hydroxide
tetrabutylammonium hydroxide
Triton-B (benzyltrimethylammonium hydroxide)
trimethyloctylammonium hydroxide
dimethyldioctylammonium hydroxide
See Examples 7 to 11.

TABLE I

THE SELECTIVE HYDROGENATION OF O-NITROANILINE

| EXAMPLE | NITROAROMATIC SUBSTRATE | ADDED BASE | NITROAROMATIC CONV. (%) | MAJOR PRODUCT IDENTITY | SELECTIVITY (%) |
|---|---|---|---|---|---|
| 4 | O-NITROANILINE | NONE | <2 | NONE | — |
| 5 | P-NITROANILINE | NONE | 98 | P-PHENYLENEDIAMINE | 94 |
| 6 | O-NITROANILINE | QUINOLINE | <2 | NONE | — |
| 7 | O-NITROANILINE | $(CH_3)_4NOH^a$ | 98 | O-PHENYLENEDIAMINE | 95 |
| 8 | O-NITROANILINE | $PhCH_2(CH_3)_3OH^b$ | 27 | O-PHENYLENEDIAMINE | 95 |
| 9 | O-NITROANILINE | $(n-C_4H_9)_4NOH$ | 98 | O-PHENYLENEDIAMINE | 94 |
| 10 | O-NITROANILINE | $(CH_3)_3(C_8H_{17})NOH^c$ | 98 | O-PHENYLENEDIAMINE | 95 |
| 11 | O-NITROANILINE | $(CH_3)_2(C_8H_{17})_2NOH^c$ | 98 | O-PHENYLENEDIAMINE | 95 |

[a] Added as 24% soln. in methanol. 0.30 M $(CH_3)_4NOH$
[b] Added as 40% soln. in methanol. 0.30 M $PhCH_2(CH_3)_3NOH$
[c] Prepared from corresponding quaternary ammonium halide salt by treatment with KOH solution

EXAMPLE 12

Hydrogenation Catalyzed by Various Ruthenium Complexes as Catalysts

Using the apparatus, hydrogenation technique and analytical methods described in Example 1, a number of ruthenium complexes, solubilized is equivolume benzene, ethanol, were employed as catalysts for the hydrogenation of o-nitroaniline. Excess tetramethylammonium hydroxide was present in all cases. O-Phenylenediamine was the major product fraction when each of the following ruthenium complexes were employed singly or as mixtures thereof, for the selective hydrogenation of o-nitroaniline, viz:

| | |
|---|---|
| Dichlorotricarbonyl-ruthenium (II) dimer | $[RuCl_2(CO)_3]_2$ |
| Dichlorodicarbonylbis-(triphenylphosphine)ruthenium (II) | $RuCl_2(CO)_2(PPh_3)_2$ |
| Ruthenium Acetylacetonate | $Ru(CH_3COCHCOCH_3)_3$ |
| Trichloronitrosylbis(triphenylphosphine) ruthenium (III) | $RuCl_3(NO)(PPh_3)_2$ |
| Hydrochlorotris(triphenylphosphine) ruthenium (II) | $RuHCl(PPh_3)_3$ |
| Trichlorobis(triphenylarsine) ruthenium (III) | $RuCl_3(AsPh_3)_2$ |
| Hydrated ruthenium (III) trichloride | $RuCl_3 \times H_2O$ |
| Ruthenium (III) acetate | $Ru(CH_3COO)_3$ |

EXAMPLE 13

Hydrogenation of Various Nitroaromatics

Using the apparatus, hydrogenation procedure and ruthenium catalyst combination of Example 1, various substituted nitroaromatic derivatives containing other functional groups were reduced to amine at 120° C. under 1200 psi initial $H_2$ pressure using a 200:1 initial ratio of $-NO_2$ to ruthenium.

The corresponding arylamine products were detected when each of the following substituted nitroaromatics were subject to selective hydrogenation, viz:
2-nitro-m-phenylenediamine
4-nitro-m-phenylenediamine
2-nitro-p-phenylenediamine
1-chloro-2-nitrobenzene
o-nitroanisole
o-nitroacetophenone As the numerous examples and the detailed disclosure of this invention indicate, the inventive process is both novel and advantageous in view of the known prior art. For example, numerous ruthenium homogeneous catalysts complexes, illustrated by $RuCl[P(C_6H_5)_3]_3$, can be used to effect the selective hydrogenation of a variety of nitroaromatic substrates containing bulky or reactive ortho-substituents. The high ratios of substrate to catalyst which may be employed minimize costs, and the hydrogenated products may be produced at consistently high conversions of nitroaromatics, as well as high selectives to the desired corresponding amine.

Finally, the instant invention lends itself to various changes, substitutions and modifications without departing from the inventive concept. For instance, a variety of quaternary alkyl and aryl ammonium hydroxide bases may be employed, in combination with said class of ruthenium homogeneous hydrogenation catalysts, to effect the desired selective reduction of a variety of hindered nitroaromatic substrates.

However, the metes and bounds of this invention can best be gleaned from an examination of the claims which follow, taken in conjunction with the preceding specification.

What is claimed is:

1. A process for selectively hydrogenating the nitro groups of mononitroaromatic substrates wherein said nitroaromatics contain one or more ortho-substituents selected from the group consisting of alkyl, halogenated alkyl, alkoxyl, acetyl, halo, substituted amino and amino substituents, and mixtures thereof, to the corresponding amines, utilizing a homogeneous ruthenium-containing catalyst complex selected from the group consisting of $RuCl_2[P(C_6H_5)_3]_3$, $[RuCl_2(CO)_3]_2$, $RuCl_2[As(C_6H_5)_3]_3$, $RuHCl[P(C_6H_5)_3]_3$, $Ru(CH_3COCHCOCH_3)_3$, $RuCl_3.XH_2O$, $RuCl_3NO[P-(C_6H_5)_3]_2$, $RuCl_2(CO)_2[P(C_6H_5)_3]_2$ and $Ru(CH_3COO)_3$ in combination with a quaternary ammonium hydroxide selected from the group consisting of tetramethylammonium hydroxide, tetraethylammonium hydroxide, benzyltrimethylammonium hydroxide, trimethyloctylammonium hydroxide and dimethyldioctylammonium hydroxide, by the process consisting essentially of, a. admixing each mole of said nitroaromatic substrates to be reduced with at least a catalytic amount of one or more of said ruthenium-containing catalyst complexes in an oxidizer-free, non-aqueous solvent media to form a reaction mixture, b. introducing into said reaction mixture an excess of quaternary ammonium hydroxide and at least sufficient hydrogen gas to hydrogenate the nitro groups of said substrates to the corresponding amines, at superatmospheric pressures ranging from about 100 psi to about 2000 psi, and c. heating said pressurized reaction mixture between about 20° to about 160° C. until said nitroaromatic substrates are reduced to amines.

2. The process of claim 1 in which said solvent medium is selected from the group consisting of aromatics, alkanols, alkyl ethers, chlorinated aliphatic hydrocarbons and mixtures thereof.

3. The process of claim 1 wherein the nitroaromatic substrate is selected from the group consisting of o-nitroaniline, N-methyl-o-nitroaniline, N,N-dimethyl-o-nitroaniline, 2-nitro-m-phenylenediamine, 4-nitro-m-phenylenediamine, 2-nitro-p-phenylenediamine, $\alpha,\alpha,\alpha$-trifluoro-o-nitrotoluene, 1-chloro-2-nitrobenzene, o-nitroanisole and o-nitroacetophenone.

* * * * *